United States Patent [19]
Skinner

[11] 3,993,085
[45] Nov. 23, 1975

[54] DENTAL FLOSS APPLICATOR

[76] Inventor: Edward T. Skinner, 2323 N. Monroe, Hutchinson, Kans. 67501

[22] Filed: June 23, 1975

[21] Appl. No.: 589,146

[52] U.S. Cl............................................... 132/92 A
[51] Int. Cl.².................................... A61C 15/00
[58] Field of Search................... 132/92 R, 92 A, 91

[56] References Cited
UNITED STATES PATENTS

| 867,264 | 10/1907 | Evans | 132/92 R |
|---|---|---|---|
| 1,417,518 | 5/1922 | Henerlau | 132/92 R |
| 3,814,114 | 6/1974 | Roberts | 132/92 A |
| 3,871,393 | 3/1975 | Wharton | 132/92 A |

*Primary Examiner*—G.E. McNeill
*Attorney, Agent, or Firm*—John H. Widdowson; Edwin H. Crabtree

[57] ABSTRACT

An improved dental floss applicator having an open faced handle for receiving a dental floss dispenser in a press fit. The applicator includes a slidable tension bar member disposed inside the handle for applying tension of the dental floss as the teeth are scrubbed. A thumb wheel advancer is attached to the applicator for advancing the floss from the dispenser as it is used.

2 Claims, 3 Drawing Figures

DENTAL FLOSS APPLICATOR

BACKGROUND OF THE INVENTION

This invention relates generally to the use of dental floss and more specifically, but not by way of limitation, to an improved dental floss applicator.

Prior art patents disclose a variety of different types of instruments for the use of dental floss. The dental floss instruments generally have a fork member with a handle and the dental floss suspended across the forked arms of the fork member. In some cases, the handles will contain a dental floss dispenser in combination with a key, knob, or advancing wheel and act together to provide a continuous flow of unused floss between the forked arms.

None of the above dental floss instruments disclose the novel combination of the improved dental floss applicator as herein described.

SUMMARY OF THE INVENTION

The subject invention eliminates the need of inserting dental floss into the mouth with the users fingers. The invention provides a dental floss applicator that is economical to use by providing a continuous supply of floss. The floss is held in a floss dispenser that can be quickly inserted or removed in the handle of the applicator. The floss is held in tension by wrapping the floss around a thumb wheel advancer. By turning the advancer the floss is fed from the floss dispenser to the forked arms. The forked arms are inserted in the mouth and the teeth are scrubbed with the floss.

The improved dental floss applicator includes an elongated fork member, fork arms holding the floss, and an open faced handle attached to the fork member. The handle receives the floss dispenser in the open face in a press fit. The floss is removed from the dispenser and fed through a notch in a slidable tension bar mounted in the handle. The tension bar provides additional tension on the floss as it is held between the forked arms. The used floss is received from the forked arms by a thumb wheel advancer. A cutter is mounted to the side of the handle for cutting the excess floss received from the advancer.

The advantages and objects of the invention will be evident from the following detailed description, when read in conjunction with the accompanying drawings, which illustrate a preferred embodiment of the invention.

DETAILED DESCRIPTION OF THE DRAWINGS

Figure 1:
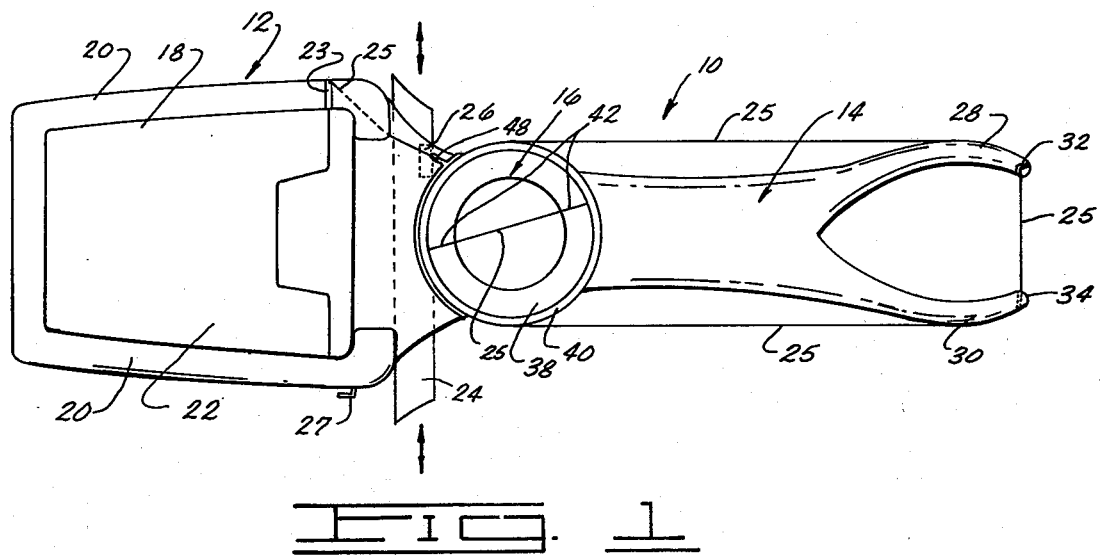
FIG. 1 is a top view of the improved dental floss applicator.

In FIG. 1 the improved dental floss applicator is designated by general reference character 10. The applicator 10 includes a handle 12, an elongated fork member 14 attached to the handle 12, and a thumb wheel advancer 16 attached to the fork member 14.

The handle 12 includes an open face portion 18 with a collar 20 therearound for receiving a dental floss dispenser 22 in a press fit. The collar 20 includes a notch 23 for receiving dental floss 25 from the dispenser 22. Inside the handle 12 is disposed a slidable tension bar 24 with a notch 26 in the side of the bar 24. The bar 24 is slidable in both directions as indicated by the arrows. Also, attached to the side of the handle 12 is a floss cutter 27 which can be used to cut floss after it has been used.

The fork member 14 includes two fork arms 28 and 30 with notches 32 and 34 at the ends of the arms for receiving the dental floss 25.

The thumb wheel advancer 16 includes an upper wheel 38 and a lower wheel 40. The upper wheel 38 has a slot 42 in the top of the wheel for securing the end of the floss 25. The floss 25 is then wound around a wheel shaft 44 shown in FIG. 2. The shaft 44 is secured to the fork member 14 and holds the wheels 38 and 40 in a fixed position as the wheels are turned about the axis of the shaft.

Figure 2:
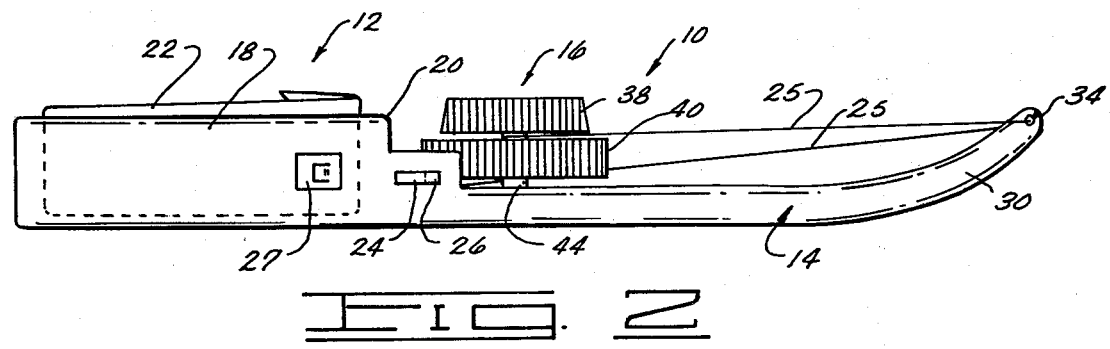
FIG. 2 is a side view of the applicator.

In FIG. 2 the floss dispenser 22 inserted inside handle 12 can be seen more clearly. In this figure the floss 25 is seen wrapped around the shaft 44 of the advancer 16.

Figure 3:
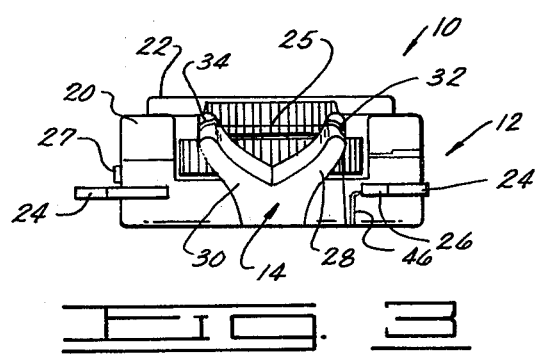
FIG. 3 is a front view of the applicator.

In FIG. 3 a notch 46 is shown in the bottom of the handle 12. Notch 46 receives the floss 25 from the tension bar member 24. In this view, the notches 32 and 34 in forked arms 28 and 30 can be seen more clearly.

In operation the improved dental floss applicator 10 is used as follows. The dental floss dispenser 22 is inserted into the open face portion 18 of handle 12. The dispenser 22 is held in a press fit against the sides of the collar 20. The dental floss 25 is taken from the side of the dispenser 22 and fed through notch 23 into a notch 48 in the handle 12. The floss is engaged inside the notch 26 of the tension bar 24. From the bar 24, the floss 25 is fed through notch 46 in the bottom of the handle 12. From here the floss 25 is fed through notches 32 and 34 in the fork arms 28 and 30. The end of the floss 25 is then secured in the slots 42 in the wheel 38. The advancer 16 can now be turned wrapping the floss 25 around the shaft 44.

The user of the floss 25 inserts the fork member 14 and fork arms 28 and 30 into the mouth. The floss 25 is inserted between the teeth and the teeth are scrubbed. The applicator 10 is removed from the mouth and the advancer 16 is turned removing the used portion of the floss 25 from between the arms 28 and 30. The applicator can now be inserted again in the mouth with unused floss. When the used floss 25 wrapped around the advancer 16 becomes excessive, it can be removed and cut by floss cutter 27.

While the teeth are being scrubbed, the tension on the floss may be decreased because the floss becomes worn or loosened. The tension on the floss can be maintained or increased by the user by merely pushing the tension bar 24 in either directions causing the floss to tighten between the two fork arms 28 and 30. This tightening of the floss 25 improves the cleaning ability of the floss 25 between the users teeth.

Changes may be made in the construction and arrangement of the parts or elements of the various embodiments as disclosed without departing from the spirit and scope of the invention as defined in the following claims.

I claim:

1. In a dental floss applicator having an elongated fork member, fork arms holding the floss therebetween, the fork member and fork arms inserted into the mouth for scrubbing the teeth with the floss, the improvement comprising:

a. a substantially rectangular shaped handle attached to the elongated fork member;

b. a "U" shaped collar formed around the periphery of said handle, said handle receiving a substantially rectangular shaped floss dispenser inside said collar and compressed against the sides thereof;

c. a slidable tension bar disposed inside said handle and positioned between the floss dispenser and the fork arms, the ends of said bar extending outwardly from the sides of said handle, said bar having a notch therein for receiving the floss as it is fed from the dispenser to the forked arms;

d. a thumb wheel advancer having a shaft attached to the front of the fork member, said thumb wheel advancer having a slot across the face of said advancer for securing the end of the floss, the floss wrapped around said shaft as the wheel advancer is turned; and e. a floss cutter attached to said handle for cutting the used floss when the floss is removed from said shaft.

2. In a dental floss applicator having an elongated fork member, said fork member holding the floss therebetween, the fork member and fork arms inserted into the mouth for scrubbing the teeth with the floss, the improvement comprising:

a. a substantially rectangular shaped handle attached to the elongated fork member;

b. a "U" shaped collar formed around the periphery of said handle, said handle receiving a substantially rectangular shaped floss dispenser inside said collar and compressed against the sides thereof;

c. a slidable tension bar disposed inside said handle and positioned between the floss dispenser and the fork arms, the ends of said bar extending outwardly from the sides of said handle, said bar having a notch therein for receiving the floss as it is fed from the dispenser to the fork arms, said bar applying tension on the floss by slidably urging the ends of said bar toward said handle;

d. a thumb wheel advancer, said wheel advancer having an upper wheel and a lower wheel mounted on a shaft attached to the front of the fork member, said upper wheel having a slot across the face thereof for securing the end of the floss, the floss wrapped around said shaft between said upper wheel and said lower wheel as said wheels are turned; and e. a floss cutter attached to said handle for cutting the used floss when the floss is removed from said shaft.

* * * * *